(12) United States Patent
Barmaimon et al.

(10) Patent No.: US 11,471,593 B2
(45) Date of Patent: Oct. 18, 2022

(54) ANGLED INTEGRATED SOFT CANNULA

(71) Applicant: FLEX LTD., Singapore (SG)

(72) Inventors: Eyal Barmaimon, Haifa (IL); Lior Shtram, Tel-Aviv (IL); Shai Finkman, Haifa (IL); Erez Levy, Atlith (IL); Nadav Cohen, Haifa (IL)

(73) Assignee: FLEX LTD., Singapore (SG)

( * ) Notice: Subject to any disclaimer, the term of this patent is extended or adjusted under 35 U.S.C. 154(b) by 517 days.

(21) Appl. No.: 16/295,811

(22) Filed: Mar. 7, 2019

(65) Prior Publication Data

US 2019/0274730 A1    Sep. 12, 2019

Related U.S. Application Data

(60) Provisional application No. 62/640,436, filed on Mar. 8, 2018.

(51) Int. Cl.
*A61B 17/34* (2006.01)
*A61M 5/158* (2006.01)
(Continued)

(52) U.S. Cl.
CPC ........ *A61M 5/158* (2013.01); *A61M 5/14248* (2013.01); *A61B 17/3431* (2013.01);
(Continued)

(58) Field of Classification Search
CPC ............ A61B 17/3439; A61B 17/3431; A61B 17/3462; A61B 17/34; A61M 5/14248; A61M 5/158; A61M 5/1723; A61M 2005/14252; A61M 2005/1581; A61M 2005/1583; A61M 2005/1585; A61M 2295/583; A61M 25/01; A61M 25/06; A61M 25/065; A61M 25/0606; A61M 25/0631
See application file for complete search history.

(56) References Cited

U.S. PATENT DOCUMENTS 5,281,218 A * 1/1994 Imran ................ A61B 18/1492
606/33
6,878,136 B2 * 4/2005 Fleury .................. A61M 5/158
128/919
(Continued)

OTHER PUBLICATIONS

Non-Final Office Action dated Aug. 20, 2020 issued in corresponding U.S. Appl. No. 16/295,799.
(Continued)

*Primary Examiner* — Erich G Herbermann
(74) *Attorney, Agent, or Firm* — Volpe Koenig (57) ABSTRACT

A device and method are disclosed for an elastic strip with a first fixed end and a second movable end, the elastic strip configured to be in at least one of a tense state and an elastic state. A release mechanism is configured to maintain the elastic strip in a tense state when the release mechanism is in a holding state, and configured to release the elastic strip when in a release state. A needle path with a first bend is provided. A rigid needle is configured to traverse a first portion of the needle path when the elastic strip is in the elastic state and a cannula is located in the needle path and configured to traverse a second portion of the needle path when the rigid needle traverses the first portion of the needle path.

8 Claims, 8 Drawing Sheets

(51) Int. Cl.
*A61M 5/142* (2006.01)
*A61M 5/172* (2006.01)

(52) U.S. Cl.
CPC ....... *A61B 17/3439* (2013.01); *A61B 17/3462* (2013.01); *A61M 5/1723* (2013.01); *A61M 2005/14252* (2013.01); *A61M 2005/1581* (2013.01); *A61M 2005/1583* (2013.01); *A61M 2005/1585* (2013.01)

(56) References Cited

U.S. PATENT DOCUMENTS

| | | | |
|---|---|---|---|
| 2002/0123740 A1* | 9/2002 | Flaherty | A61M 5/1452 604/890.1 |
| 2006/0142698 A1* | 6/2006 | Ethelfeld | A61B 5/6848 604/157 |
| 2009/0048563 A1 | 2/2009 | Ethelfeld et al. | |
| 2015/0196719 A1 | 7/2015 | Uchiyama | |
| 2016/0361013 A1 | 12/2016 | Schmid | |
| 2017/0043133 A1 | 2/2017 | Amano et al. | |
| 2017/0119959 A1 | 5/2017 | Cole et al. | |

OTHER PUBLICATIONS

International Search Report and Written Opinion dated Jul. 2, 2019 issued in corresponding international patent application No. PCT/IB2019/051907.
International Search Report and Written Opinion dated Jul. 10, 2019 issued in corresponding international patent application No. PCT/IB2019/051908.

* cited by examiner

ANGLED INTEGRATED SOFT CANNULA

This application claims the benefit of U.S. Provisional Application No. 62/640,436 having a filing date of Mar. 8, 2018, which is incorporated by reference as if fully set forth.

BACKGROUND

There is a strong market need for an apparatus that can enable the subcutaneous self-administration of solutions such as medication in a wearable format factor. For instance, the treatment of diabetes requires the subcutaneous delivery of insulin. As a result, wearable pumps that deliver a medication to a patient may be used to administer such solutions. These pumps may incorporate the medication, pumping mechanism, and infusion set into a patch that attaches to a patient's skin, thus eliminating the need for external systems.

Patients may wear patch pumps for a prolonged period of time and, accordingly, patient comfort and ease of use is a consideration in the design and manufacturing of such patch pumps.

SUMMARY

A device and method are disclosed for an elastic strip with a first fixed end and a second movable end, the elastic strip configured to be in at least one of a tense state and an elastic state. A release mechanism is configured to maintain the elastic strip in a tense state when the release mechanism is in a holding state, and configured to release the elastic strip when in a release state. A needle path with a first bend is provided. A rigid needle is configured to traverse a first portion of the needle path when the elastic strip is in the elastic state and a cannula is located in the needle path and configured to traverse a second portion of the needle path when the rigid needle traverses the first portion of the needle path.

BRIEF DESCRIPTION OF THE DRAWINGS

A more detailed understanding may be had from the following description, given by way of example in conjunction with the accompanying drawings wherein.

DETAILED DESCRIPTION

Examples of different pumps and needle insertion mechanism implementations will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

Below are described an apparatus and methods for delivering solutions such as pharmaceutical drugs and/or biologics to a patient. The apparatus and methods may allow for prescription or standard off-the-shelf drug cartridges to be utilized without compromising the sterility of the solution. This may enable a patient to self-administer a solution in a self-contained wearable patch pump form factor that is cost effective and comfortable to wear. The disclosure subject matter provided herein may allow the manufacturing and use of a patch pump that is small enough in size to be comfortable to wear.

Figure 1A:
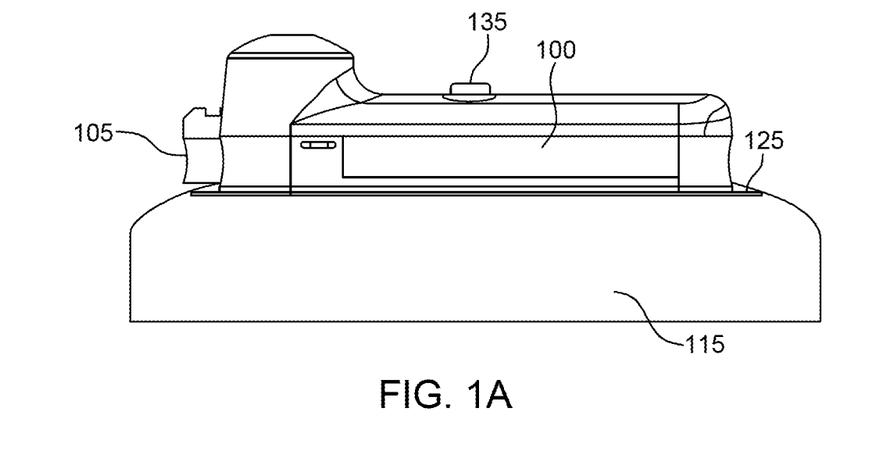
FIG. 1A is a graphic depiction of a patch pump on a user.

FIG. 1A is a graphic depiction of a patch pump 100 on a patient 115. The patch pump 100 includes a base 125 that contacts the patient's skin. In some embodiments, the base 125 includes an adhesive liner that affixes the patch pump 100 to the patient 115. The patch pump 100 may further include a user flow control switch 135. The user flow control switch 135 may enable a user to pause and control the flow rate of a solution. The patch pump 100 further includes a start button 105 that may be pressed by a user to cause a cannula and/or needle to be inserted into the patient and the solution to flow from a drug container 130 through the cannula and/or needle into the patient.

Figure 1B:
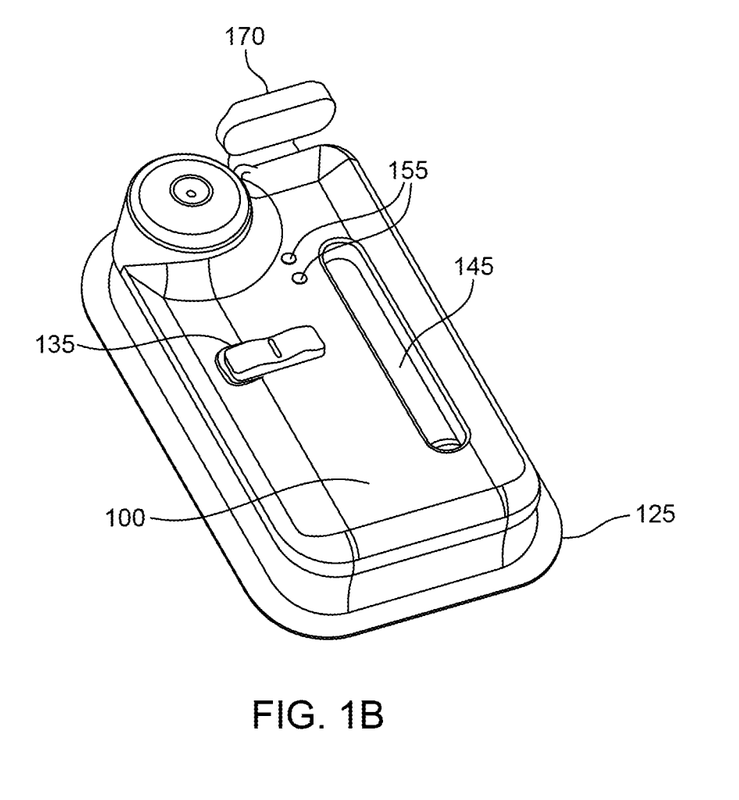
FIG. 1B is a graphic depiction of the outer casing of an embodiment of a patch pump.

As shown in FIG. 1B, the patch pump 100 may further include a drug viewing window 145. This viewing window may enable a user to view the amount of a solution that remains in the drug container 130. The patch pump 100 may also include one or more visual indicators 155. The visual indicators 155 provide feedback on the operational status of the system. The operational status of the system may include warnings such as an over/under temperature warning, drug expiration warning and over/under pressure warning. In addition, the operational status may include information indicating that the drug is being administered, how much time is remaining for the drug dosage to be completed and the current flow rate. The visual indicators may include LEDS, LCD displays or other similar display technologies known in the art. The information that is displayed by visual indicators may also be wirelessly transmitted to a mobile computing device such as a smart phone utilizing any of the wireless communication methods known in the art.

The patch pump 100 may further include a removable safety 170. The removable safety mechanically engages the start button 105 and prohibits the start button 105 from being involuntary pressed.

Figure 1C:
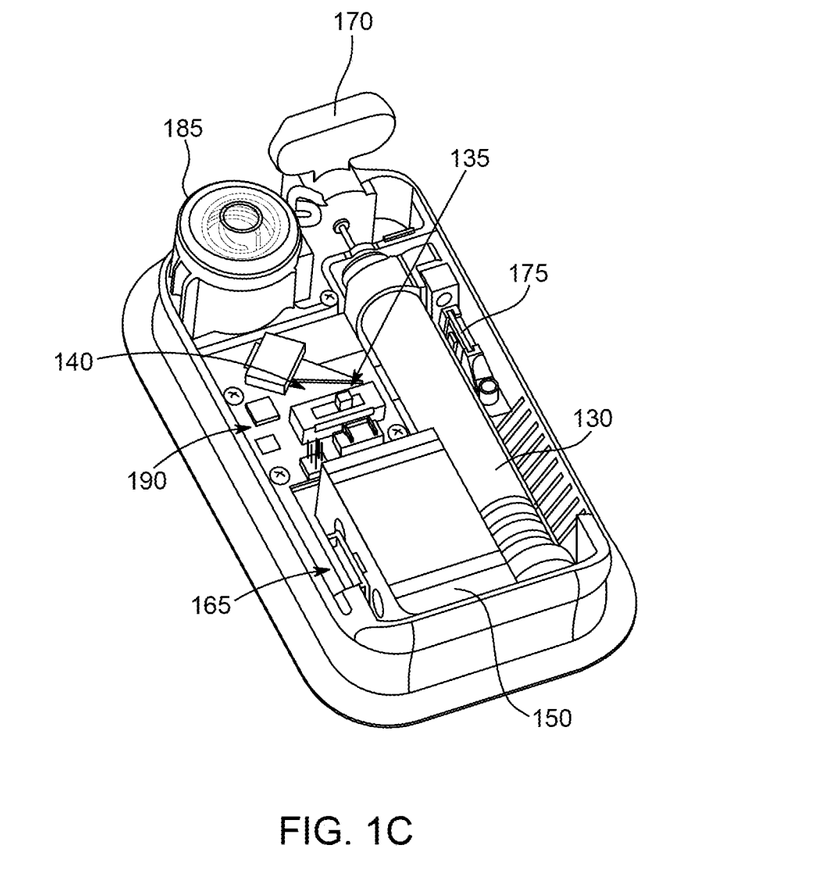
FIG. 1C is a graphic depiction of an embodiment of a patch pump with the outer casing removed.

FIG. 10 shows additional components of a patch pump 100. The patch pump 100 may also include a needle insertion component 185 that is mechanically connected to the start button 105. In addition, the patch pump 100 includes an electronic circuit board 140 that includes control circuitry for the visual indicators 155, user flow control switch 135 and a pressurization system 150. In addition, the electronic circuit board 140 may be communicatively connected to one or more sensors. These sensors may include pressure sensor 165 and proximity sensor 175. The electronic circuit board 140 may also include a memory 190. The memory 190 may store dosing instructions for the administration of the solution. In addition, the memory 190 may also store information regarding the administration of the solution. This information IT may include, time, date, and flow rate when the solution was administered. The electronic circuit board 140 may control the visual indicators 155 and the pressurization system 150 based on the information stored in the memory and the feedback from the sensors. The electronic circuit board 140 may include a communication module that enables the transmission of information stored in the memory 190 to a wireless computing device. In addition, the communication module may also receive updated dosing instructions that are subsequently stored in the memory 190.

A device, such as a patch pump, configured in accordance with the disclosed subject matter may consume a smaller footprint than traditional patch pumps and/or needle mechanisms. Such a device may be configured to allow the movement of a needle in a first plane and the needle may cause the movement of a cannula in a second plane. As an example, a needle may be pushed by an elastic strip from right to left on a horizontal plane and a distal end of the needle may then push a cannula towards the bottom, in a vertical plane. The movement in two different planes may allow the device to be smaller than if the movement of the needle and the cannula was in the same plane.

As disclosed herein, such a device may include an elastic strip with a first fixed end and a second movable end. The elastic strip may be cured (e.g., annealed) in a forming state, which is, for example, a cured compressed state (e.g., V-shape) such that any deviation of the elastic strip may cause the elastic strip to be in a tense state such that its properties cause a force (e.g., potential energy) to be generated in the direction(s) that cause the elastic strip to return to the forming state. A release mechanism may hold the elastic strip in a tense state such that it is configured to maintain the elastic strip in a tense state when the release mechanism is in a holding state. The release mechanism may be configured to release the elastic strip when in a release state, based on an activation mechanism. A needle path with a first bend is provided. A rigid needle may be attached to an end of the elastic strip such that the rigid needle is configured to traverse a first portion of the needle path when the elastic strip changes from a tense state to an elastic state. The movement of the rigid needle across the needle path may cause an end of the rigid needle distal from the elastic strip to apply a force on a cannula that is located in the needle path. As a result of the force, the cannula may traverse a second portion of the needle path when the rigid needle traverses the first portion of the needle path.

Figure 2A:
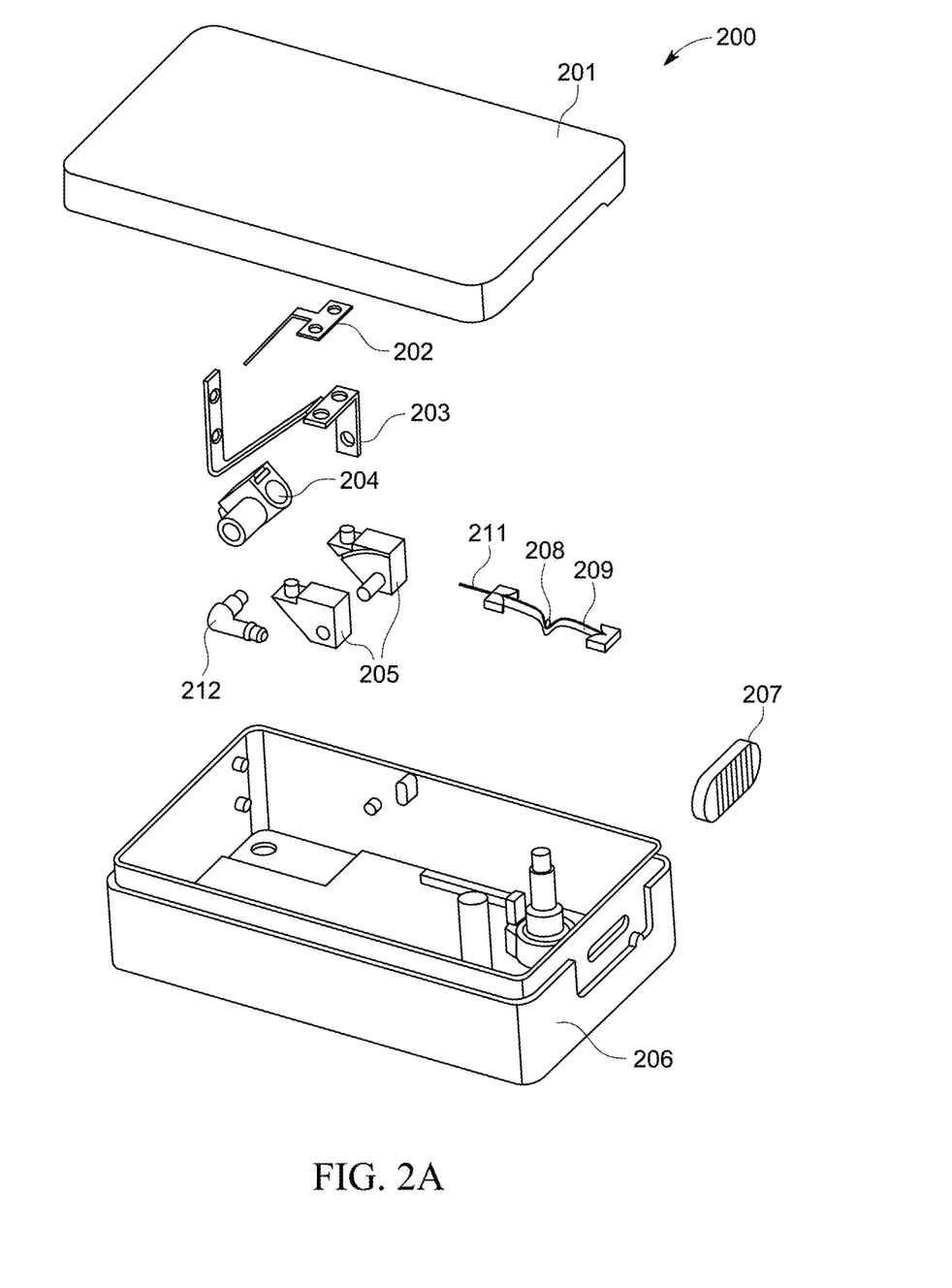
FIG. 2A is a graphical depiction of an exploded view of an insertion mechanism.

FIG. 2A is a graphic depiction of an exploded view of an insertion mechanism 200. The insertion mechanism 200 may be included in the needle insertion component 185 of patch pump 100, as shown in FIGS. 1A-C or may be part of a different patch pump or other solution delivery mechanism which requires the use of a needle and/or cannula. Accordingly, the insertion mechanism 200 may be configured to operate with the components shown in FIGS. 1A-C or, alternatively, may be configured to operate with a subset of the components shown in FIG. 1A-C or none of the components shown in FIGS. 1A-C. Patch pumps with different or modified components then those shown in FIGS. 1A-C may be used with insertion mechanism 200.

FIG. 2A shows an exploded view of a insertion mechanism 200, which includes a top cover 201, a rigid needle 210, a carriage stopper 202, a rail 203, a cannula carriage 204, plate attachment 225, a cannula 211, a wire guide 205, a fitting component 212, a button 207, an elastic strip 209, a release mechanism 208, and a bottom cover 206. It will be understood that one or more components shown in FIG. 2A may not be present to implement the subject matter disclosed herein. Additionally, it will be understood that one or more additional components, not shown in FIG. 2A may be provided to implement the subject matter disclosed herein.

Figure 2B:
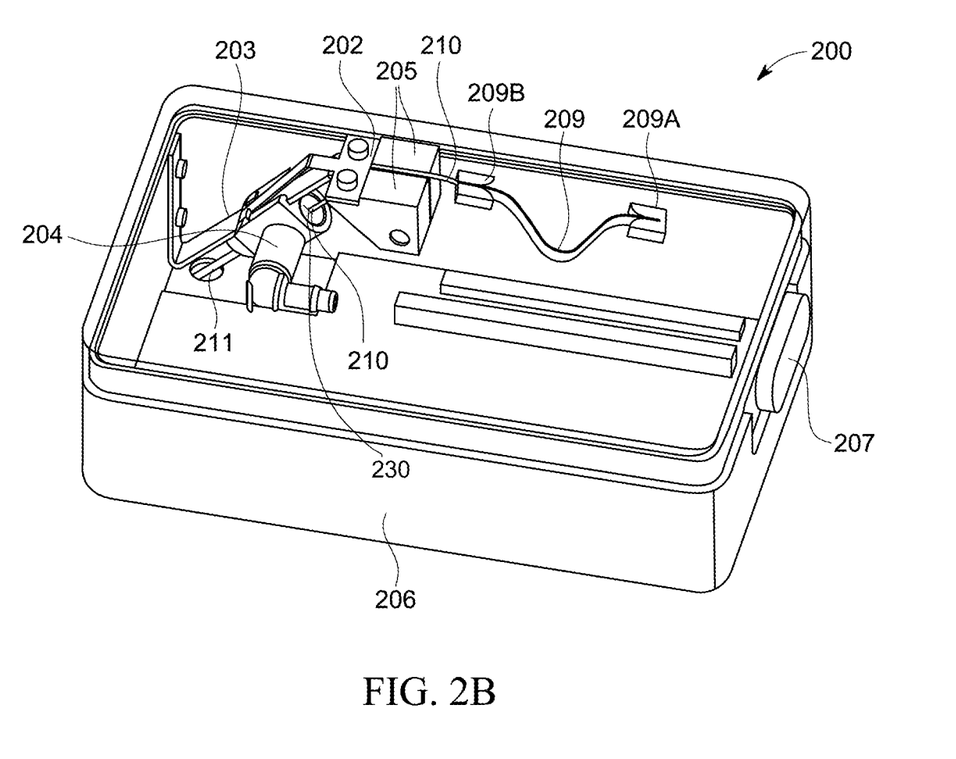
FIG. 2B is a graphical depiction of an assembled insertion mechanism.

The insertion mechanism 200 of FIG. 2A may be part of a patch pump, such as patch pump 100, of FIGS. 1A-1C or may be separate and apart from a patch pump. As an example, the insertion mechanism 200 of FIG. 2A may be inserted into a patch pump that may be configured to use an assembled version of the insertion mechanism 200 (e.g., as shown in FIG. 2B, as further disclosed herein) as a single e use device. According to this example, the patch pump or user may discard the needle mechanism 200 after each use an replace the needle mechanism 200 with a new needle mechanism 200 for each use.

The top cover 201 and bottom cover 206 may be made of any applicable material configured to provide needle insertion, and may include plastic, metal, or a hybrid collection of materials. According to an implementation, the top cover 201 and/or bottom cover 206 may be a single component or may be joined via an adhesive or one or more mechanical connectors (not shown).

Figure 2C:
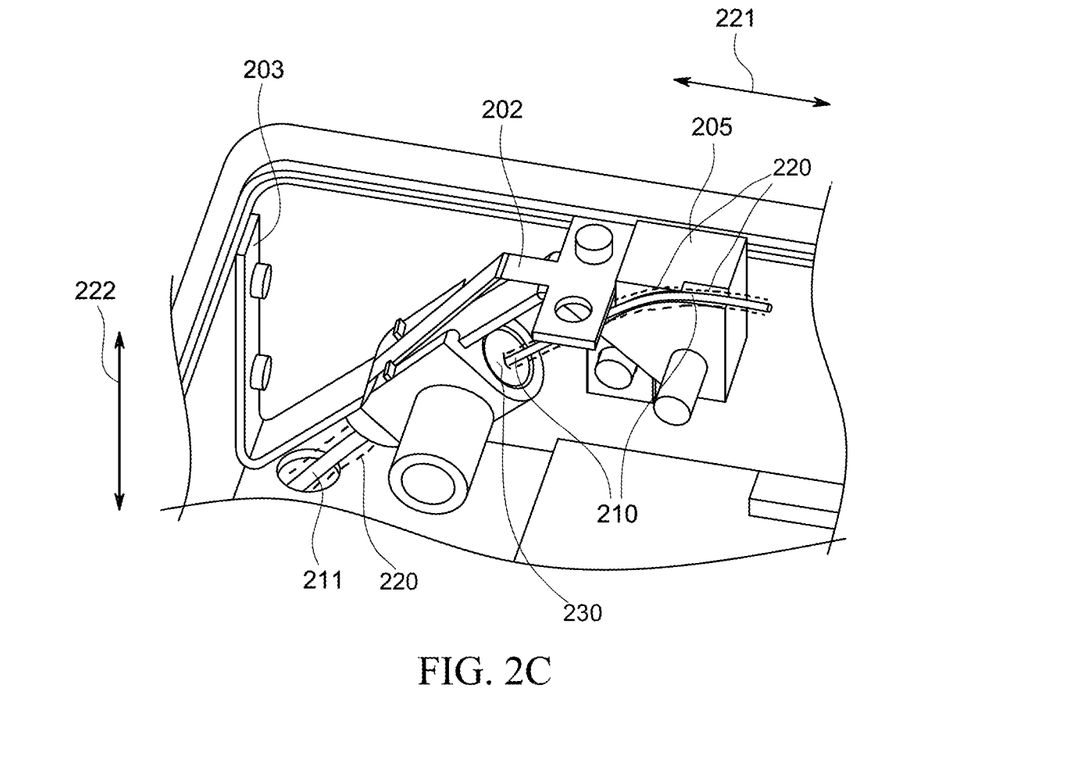
FIG. 2C is another graphical depiction of an assembled insertion mechanism.

The rigid needle 210 may be composed of any applicable material that enables the rigid needle 210 to maintain a bend along a needle path 220, as shown in FIG. 2C. Additionally, a rigid needle 210 may be composed of any applicable material that enables the rigid needle 210 to cause the cannula 211 to be pushed in a desired direction, as further disclosed herein. As non-limiting examples, a rigid needle 210 may be composed of nitinol (Ni—Ti), stainless steel, or the like. It will be understood that, according to one or more implementations, the rigid needle 210 may be bendable, in accordance with the subject matter herein.

The cannula 211 may be a tube that is configured to insert into a vein or body cavity to administer a solution, drain fluid, to insert a surgical instrument, or to gather data.

The cannula carriage 204 may be a component that is attached to the cannula 211 and facilitates the movement of the cannula 211 when the rigid needle 210 applies a force on the cannula 211 or cannula carriage 204 such that the force causes the cannula 211 and/or cannula carriage 204 to move along a needle path 220. The cannula carriage 204 may be configured to traverse along the needle path 220 and may be guided or supported by the rail 203. The cannula carriage may detach from the cannula 211 as the cannula 211 is inserted into a user or may remain attached to the cannula 211 after the cannula 211 is inserted into a user.

The carriage stopper 202 may be configured to facilitate the movement of the cannula carriage 204 as the cannula carriage 204 moves along the rail 203. The carriage stopper 202 may facilitate the movement of the cannula carriage 204 by mechanically or electronically stopping the cannula carriage 204 from moving past a threshold. The threshold may be pre-determined or may be determined in relation to a force applied by the rigid needle 210, as further disclosed herein. Further, the carriage stopper 202 may be configured to prevent the cannula carriage 204 and/or cannula 211 from retracting towards a first or original position, as a rigid needle 210 retracts, due to an elastic strip 209 changing from an elastic state to a forming state, as disclosed herein.

One or more wire guides 205 may form at least a part of a needle path 220 such that they guide the rigid needle 210 along a bend towards the cannula 211/cannula carriage 204. As further shown in FIG. 2B, the wire guides 205 may include a curving surface that curves from the original plane where the rigid needle 210 is connected to the elastic strip 209 towards the bottom of the insertion mechanism 200. The needle path 220, created at least in part by the wire guides 205 may be slightly larger than the rigid needle 210. The dimensions of the needle path 220 may be determined based on the size or diameter of the rigid needle 210 such that the needle path 220 is large enough to allow the rigid needle 210 to move along the needle path 220. Additionally, the dimensions of the needle path 220 may be small enough such that when the rigid needle 210 moves along/traverses the needle path 220, it does not experience any unintended movement or shaking within the needle path 220.

As disclosed herein, the needle path 220 may be non-linear such that it may contain a curve at least at the wire guides 205. It will be understood that although a single curve at the wire guides 205 is described herein, the needle path 220 may contain two or more curves in order to enable a rigid needle 210 to traverse an intended path. The curve at the wire guides 205 may alter a direction of the needle path 220 from a first direction in a first plane to a second direction in a second plane. As shown in FIG. 2B, the needle path 220 may begin in a first substantially horizontal plane 221. The needle path 220 may change directions at curve wire guides 205 to a substantially vertical plane 222 (shown by the location of the cannula 211). It will be understood that although a substantially 90-degree change within a Z plane is shown in FIG. 2B, the needle path 220 may alter a direction at any angel and within any plane. As an example, the needle path 220 may alter a direction at a 60-degree angle or, alternatively, the needle path 220 may alter a direction at a 30-degree angle.

According to an implementation, an insertion mechanism 200 that includes a needle path with a 90-degree change in direction may occupy a smaller footprint in a first dimension than a needle path with a smaller (e.g., 60 degree) change in direction. For example, a insertion mechanism 200 with a needle path with a 90-degree change in direction may be shorter in length than a similar insertion mechanism 200 with a needle path with a 60-degree change in direction. However, a insertion mechanism 200 that includes a needle path with a 90-degree change in direction may occupy a larger footprint in a second dimension than a needle path with a smaller (e.g., 60 degree) change in direction. Continuing the example, the insertion mechanism 200 with a needle path with a 90-degree change in direction may be lower in height than a similar insertion mechanism 200 with a needle path with a 60-degree change in direction. The angle may be determined based on the use case for the needle insertion mechanism. For example, certain use cases may require a patch pump to be smaller in height and, thus, may result in a lower angle. As another example, certain use cases may require a patch pump to be smaller in width and, thus, may result in a larger angle.

A rigid needle 210 may be inserted into a needle path 220 during the manufacturing process such as after some of the components of the insertion mechanism 200 have been assembled. Alternatively, according to an implementation, a rigid needle 210 may be inserted into a needle path 220 after the insertion mechanism 200 has been fully assembled. According to an implementation, a rigid needle 210 may be replaced or removed and reinserted into the needle path 220. The rigid needle 210 may have a diameter that is smaller than the diameter of the cannula 211.

A plate attachment 230, as shown in FIGS. 2B and 2C, may be affixed to the rigid needle 210. The plate attachment 230 may be affixed such that the plate attachment 230 is part of an end of the rigid needle 210 or may be attached to the rigid needle 210 via any applicable mechanical, adhesive, or other attaching technique. The plate attachment 230 may be configured to apply a force onto the cannula carriage 204 to move the cannula carriage 204 and/or the cannula 211 from a first position to a second position along the needle path 220. The movement of the rigid needle 210 as the elastic strip 209 changes from a tense state to an elastic state may cause the plate attachment 230 to move from a first position to a second position along the needle path 220. As disclosed above, the movement of the plate attachment 230 may be caused by the elastic strip changing to an elastic state and applying a force to the rigid needle 210, causing the rigid needle 210 to move from a first position to a second position and, thus, causing the plate attachment 230 to move from a first position to a second position.

According to an implementation, the plate attachment 230 moves with the rigid needle 210 and may retract from a second plate position to its first plate position when the rigid needle 210 moves from a second position back to its first position as the elastic strip 209 changes from an elastic state to a forming state, as disclosed herein.

According to an implementation, the plate attachment 230 may detach from the rigid needle 210 and may remain in contact with the carrier carriage 204.

A fitting component 212 may be provided and may facilitate the connection of a fluid path (not shown) to the cannula 211 via the cannula carriage 204.

An elastic strip 209 may be provided. The elastic strip 209 may composed of any super elastic material and/or may be a shape-memory alloy and may be composed of materials such as, but not limited to Ni—Ti, Cu—Al—Ni, Fe—Mn—Si, Cu—Zn—Al, or Cu—Al—Ni, or a combination thereof. The elastic strip 209 may have at least three states associated with it: a forming state, a tense state, and an elastic state. The forming state may be the state in which the elastic strip 209 is formed. The elastic strip 209 may be formed in a certain shape, such as a V-shape, as further disclosed herein and shown in FIGS. 2A, 2B, 2D and 2E. The elastic strip 209 may at least in part by formed using a curing process such as an annealing process. It will be understood that the V-shape is just an example, and the shape my be an other applicable shape such as one that is closer the shape of a "U" or any other shape where the elastic strip 209 is not fully extended.

The elastic strip 209 may have properties such that if has no force is applied to the elastic strip 209, it will remain in a first state, such as the forming state (e.g., a V-shape). According to the subject matter disclosed herein, a force may be applied to the elastic strip 209 (e.g., via a release mechanism 208, as further disclosed herein). The force may cause the elastic strip 209 to change from the forming state to a second state, such as a tense state such that, as a result of the force, a potential energy is built up in the elastic strip 209 in the direction of the forming state. To clarify, the potential energy may be in the direction such that, absent the force, the elastic strip 209 would return to the forming state. According to the implementations disclosed herein, the tense state may be one in which the elastic strip 209 is shaped beyond its fully extended length, such as, for example, if the V-shape of the forming state is reversed so that the V-shape is in the opposite direction while in the tense state.

The elastic strip 209 may change from a tense state to an elastic state when the force (e.g., release mechanism 208) is reduced or removed from the elastic strip 209. Notably, when the force is reduced or removed, the elastic strip 209 may snap back towards the forming state. The elastic state may be the state that the elastic strip 209 is in between when it is in the tense state and the forming state. As an example, the release mechanism 208 may hold the elastic strip 209 in a V-shape that is opposite to the V-shape that the elastic strip is in when in its forming state. Upon removal of the force by the release mechanism 208, the elastic strip 209 may extend to its full length, in its elastic state, as it snaps back to its forming state V-shape. As further disclosed herein, this elastic state when the elastic strip 209 extends to its full length may cause the rigid needle 210, that is attached to a movable end of the elastic strip 209, to move along the needle path 220, and apply a force on the cannula 209/cannula carriage 204.

Figure 2D:
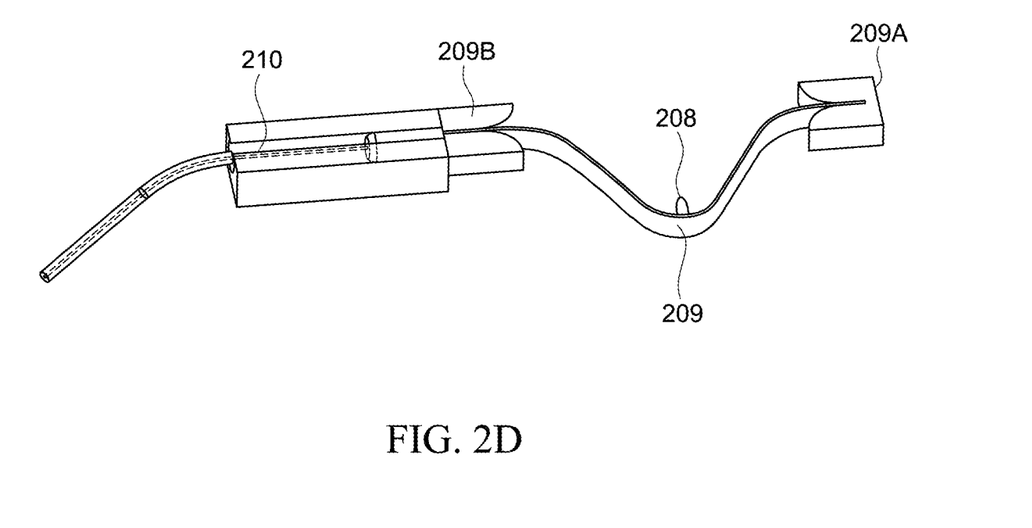
FIG. 2D is a graphical depiction of an elastic strip.

The release mechanism 208, as shown in FIGS. 2A and 2D may be any mechanical or electronic mechanism that is configured to hold the elastic strip 209 in a tense state. The release mechanism 208 may be a hook, a stopper, a pincher or the like such that it applies a force on the elastic strip 209 keeping the elastic strip 209 in a tense state until the release mechanism 208 is released. Accordingly, the release mechanism 208 may be configured to apply an amount of force at least equal to the force generated by the potential energy generated by the elastic strip 209 in the tense state. The release mechanism 208 may be in a holding state while the release mechanism 208 applies a force on the elastic strip 209, keeping the elastic strip 209 in a tense state. The release mechanism 208 may be in a release state when it is not in a holding state such that when the release mechanism 208 is no longer applying a force to keep the elastic strip in a tense state.

The release mechanism 208 may change from a holding state to a release state such that it no longer applies a force to keep the elastic strip 209 in a tense state. As disclosed herein, the release mechanism 208 may be any mechanism configured to keep the elastic strip 209 in a tense state. A hook release mechanism 208 may be in the shape of a hook such that it applies a force, via contact with the elastic strip 209, in the opposite direction of the force applied by the potential energy of the elastic strip 209. The hook release mechanism 208 may release by removing the hook such that it no longer contacts the elastic strip 209.

A stopper release mechanism 208 may be a physical bump or pin that it applies a force, via contact with the elastic strip 209, in the opposite direction of the force applied by the potential energy of the elastic strip 209. The stopper release mechanism 208 may release by moving the stopper release mechanism 208 such that it no longer contacts the elastic strip 209 or partially contacts the elastic strip 209.

A pincher release mechanism 208 may use one or more pinching components to hold the elastic strip 209 based on the friction or contact created by the pincher release mechanism 208 on the elastic strip 209. The pincher release mechanism 208 may release by removing all or at least part of the pinching force applied on the elastic strip 209 (e.g., by opening the pinching components).

The button 207 may be an electrical or mechanical activation mechanism that may be user activated or may be activated based on a signal. Activation of the button 207 may cause the release mechanism 208 to release such that the elastic strip 209 changes from a tense state to an elastic state as a result of releasing the release mechanism 208. It will be understood that button 207 may be part of a patch pump, such as patch pump 100 of FIGS. 1A-1C.

FIG. 2B shows an assembled version of insertion mechanism 200. A shown, the elastic strip 209 may have a first fixed end 209A and a movable end 209B. The movable end 209B may move in the direction of the wire guides 205 when the elastic strip 209 changes from a tense state, as shown in FIG. 2B, to an elastic state such that the elastic strip 209 moves in the direction of the shown in FIG. 2B. As the elastic strip 209 changes from a tense state to an elastic state, the movable end 209B may extend towards the wire guides 205 such that a rigid needle 210 attached to the movable end of the elastic strip 209 traverses a first portion of the needle path 220. The amount that the rigid needle 210 traverses the first portion of the needle path 220 may be the same as or be proportional to the extension of the elastic strip 209 during the change from the tense state to the elastic state. As an example, the elastic strip 209 may be in a V-shape while in a tense state. Upon release by a release mechanism, as shown in FIG. 2A, the elastic strip 209 may change to an elastic state which is an I-shape. The I-shape may be a materially full extension of the elastic strip 209 and correspond to a substantially full length of the elastic strip 209 in the same plane that the elastic strip 209 occupies in its tense state.

As shown in FIG. 2B and FIG. 2C, the rigid needle 210 may be in contact with a cannula 211 or cannula carriage 204. According to an implementation, the rigid needle 210 may not be in contact with the cannula 211 or cannula carriage 204 while the elastic strip 209 is in a tense state. The rigid needle 210 may come into contact with the cannula 211 or cannula carriage 204 when the elastic strip 209 changes from the tense state to the elastic state. Notably, as shown in FIGS. 2B and 2C, the rigid needle 210 may curve along a needle path 220 created in part by the wire guides 205 such that a first end of the rigid needle 210 connected to the movable end 209B of the elastic strip 209 is in a first plane and a second end of the rigid needle 210 distal to the first end of the rigid needle 210 is in a second plane. As a visual example, the first end of the rigid needle 210 may be in a plane parallel to the bottom cover 206 and the second end of the rigid needle 210 may be a an angle between 30 degrees and 90 degrees to the bottom cover 206.

As shown in FIGS. 2B and 2C, the second end of the rigid needle 210 may be in contact with the cannula 211 or cannula carriage 204. According to an implementation, the rigid needle 210 may be in contact with the cannula 211 through the cannula carriage 204. According to another implementation, the rigid needle 210 may be in contact with the cannula carriage 204 that is in contact with the cannula 211. The rigid needle 210 may traverse at least a first portion of the needle path 220 created in part by the wire guides 205, as a result of the elastic strip 209 changing from a tense state to an elastic state. Notably, the rigid needle 210 may be configured to remain rigid while traversing through the needle path 205.

The movement of the rigid needle 210 may apply a force onto the cannula 211 or cannula carriage 204, which applies a force on the cannula 211. As a result of the force applied by the rigid needle 210, the cannula 211 may traverse a second portion of the needle path 220. The cannula may exit a surface of the insertion mechanism (e.g., the bottom cover 206) and penetrate the skin of a user.

The elastic strip 209 may change from an elastic state to a forming state. Changing to the forming state may cause the elastic strip 209 to be in a shape substantially opposite of the shape of the elastic strip 209 in the tense state. As an example, the elastic strip 209 may be in a V-shape while in a tense state. The elastic strip 209 may change from the tense state to an elastic state, using the potential energy stored while in the tense state, upon a release by release mechanism 208, and may be in a I-shape while in the elastic state. The elastic strip 209 may change from the elastic state to a forming state, using potential energy and kinetic energy, and be in a V-shape that is opposite of the V-shape while the elastic strip 209 is in the tense state.

As the elastic strip 209 changes from an elastic state, where the elastic strip 209 is substantially fully extended, to a forming state, the rigid needle 210 may retract along the needle path 220. The rigid needle 210 may retract such that the first end of the rigid needle 210, which is attached to the movable end of the elastic strip 209, moves in a direction away from the wire guides 205. Note that the cannula 211 may not retract as a result of the retraction of the rigid needle 210. The cannula 211 may remain in the position that it reached while the elastic strip 209 was in the elastic state (e.g., penetrating the skin of a user outside of the insertion mechanism 200.

FIG. 2D shows a simplified version of the elastic strip 209, movable end 209B, fixed end 209A, and rigid needle 210. Elastic strip 209 is shown in a tense state held in place by release mechanism 208. The movable end 209B is configured to extend towards the direction of the rigid needle 210 when the elastic strip 209 changes from a tense state to an elastic state, as disclosed herein.

Figure 2E:
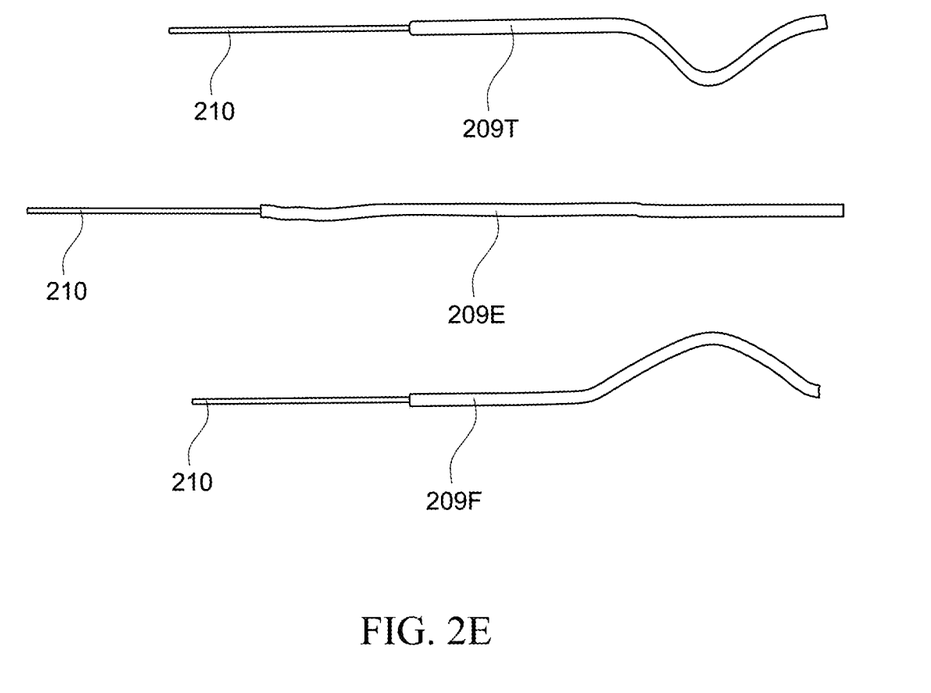
FIG. 2E is a graphical depiction of an elastic strip in different states.

FIG. 2E shows the tense state, elastic state, and forming state of an example elastic strip 209. The elastic strip 209T of FIG. 2E may correspond to an elastic strip in a tense state. The elastic strip 209T may remain in the tense state as a result of a release mechanism (not shown) that holds the elastic strip 209T in the tense state.

Upon release of the release mechanism, the elastic strip may change to the elastic state, as disclosed herein, and shown in by elastic strip 209E. Notably, the elastic strip 209E may be a substantially fully extended state of the an elastic strip such that it causes a rigid needle 210 attached to its movable end to traverse a distance determined by the extension, as shown by elastic strip 209E and the rigid needle 210 attached to it.

An elastic strip may further continue to change states to a forming state, as shown by elastic strip 209F. The forming state may be the state in which the elastic strip is cured during the formation of the elastic strip. It may be cured using any applicable curing process such as, but not limited to, an annealing process.

Figure 3:
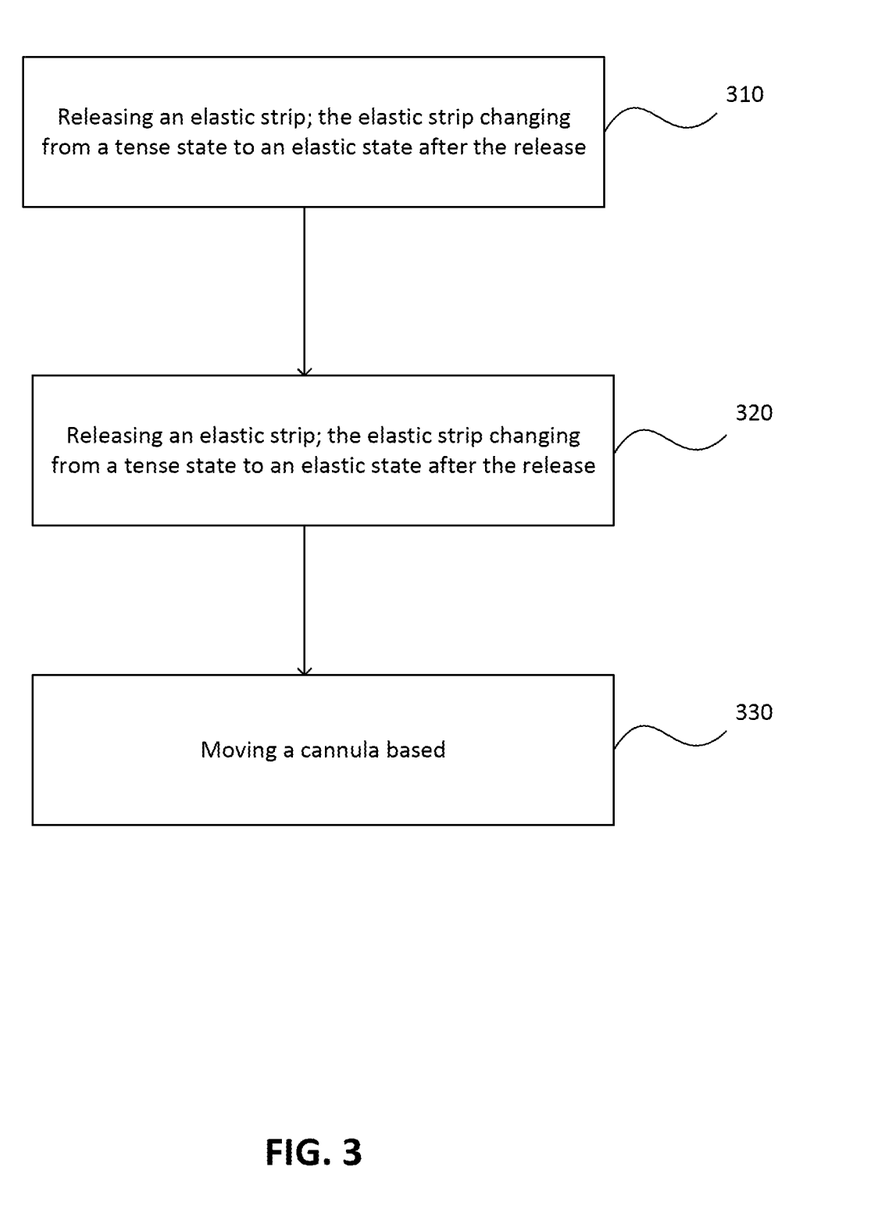
FIG. 3 is a flowchart for inserting a cannula into a user's skin by using an elastic strip.

FIG. 3 shows an example flowchart for inserting a cannula into a user based on techniques disclosed herein. The cannula may be inserted into a user's skin after exiting an insertion mechanism that includes an elastic strip. At 310, the elastic strip (such as elastic strip 209 of FIGS. 2A, 2B, 2D and 2E) is released such that it changes from a tense state to an elastic state. The elastic strip may be released based on a release mechanism (such as release mechanism 208 of FIG. 2) changing from a holding state to a release state. The release mechanism may change from a holding state to a release state based on an activation mechanism (e.g., via the push of button such as button 207 of FIG. 2A).

The elastic strip may include a movable end and a fixed end, as disclosed herein. Upon release by the release mechanism, the elastic strip may change from a tense state to an elastic state such that the elastic strip's movable end traverses a distance determined by the change in length of the elastic strip from the tense state to the elastic state. A rigid needle (such as rigid needle 210 of FIGS. 2A-2E) may be attached to the movable end of the elastic strip.

At step 320 of FIG. 3, the rigid needle may move along a needle path (such as needle path 220 of FIGS. 2B and 2C) when the elastic strip changes from the tense state to the elastic state. The distance that the rigid needle moves along the needle path may be the same as or proportional to the change in length, along a given plane, of the elastic strip between its tense state and its elastic state.

The rigid needle may apply a force onto a cannula (such as cannula 211 of FIG. 2A-2C) or cannula carriage (such as cannula carriage 204 of FIGS. 2A-2C) based on the movement of the rigid needle along the needle path. At step 330, the cannula may move along a portion of the needle path (such as the needle path 220 of FIGS. 2B and 2C) as a result of the force applied by the rigid needle onto the cannula or cannula carriage. The cannula may move a distance that is the same as or proportionate to the distance that the rigid needle transverses along the needle path. The cannula may exit the insertion mechanism. Notably, a first end of the rigid needle, connected to a movable end of an elastic strip, may move along a first plane (e.g., a horizontal plane) and the cannula may exit the insertion mechanism along a different plane (e.g., a plane between 30 and 90 degrees to the horizontal plane). Such change in planes may allow for the insertion mechanism to be provided in a smaller form factor than if the rigid needle and cannula moved within the same plane.

The rigid needle (such as rigid needle 210 of FIGS. 2A-2E) may retract back along a needle path (such as needle path 220 of FIGS. 2B and 2C) as an elastic strip (such as elastic strip 209 of FIGS. 2A, 2B, 2D, and 2E) connected to the rigid needle changes from an elastic state (e.g., an I-shape) to a forming state (e.g., a V-shape). A cannula (such as cannula 211 of FIGS. 2A-2D) and/or cannula carriage (such as cannula carriage 204 of FIGS. 2A-2D) may remain in the position that it moved to while the elastic strip was in an elastic state.

Although features and elements are described above in particular combinations, one of ordinary skill in the art will appreciate that each feature or element can be used alone or in any combination with the other features and elements.

What is claimed is:

1. A device comprising: an elongate elastic strip with a fixed end, separated from a movable end by a deformable intermediate portion having a first curved form in a cured, resting, state defining a forming state; the deformable intermediate portion configured to deform to a second curved form defining a tense state when the deformable intermediate portion is subjected to a force applied in a direction perpendicular to a longitudinal axis of the elongate elastic strip; and in response to removal of the force from the deformable intermediate portion, returning to the forming state from the tense state in a transition that defines an elastic state wherein the deformable intermediate portion deforms from the second curved form to a linear form, thereby causing extension of the movable end, whereinafter the deformable intermediate portion deforms from the linear form to the first curved form, thereby causing retraction of the movable end,
   a release mechanism configured to connect to the deformable intermediate portion to apply the force in the direction perpendicular to the longitudinal axis to maintain the deformable intermediate portion in the tense state;
   a needle path with a first bend;
   a rigid needle disposed in the needle path and attached to the movable end, the rigid needle configured to traverse a first portion of the needle path responsive to the extension of the movable end in the elastic state; and
   a cannula disposed in the needle path and coupled to the rigid needle to traverse a second portion of the needle path responsive to the rigid needle traversing the first portion of the needle path.

2. The device of claim 1, wherein the elastic strip is in a V-shape when in the tense state.

3. The device of claim 1, further comprising an activation mechanism, the activation mechanism configured to activate the release mechanism.

4. The device of claim 3, wherein the activation mechanism is at least one of electronic and mechanical.

5. The device of claim 1, wherein the release mechanism is at least one of electronic and mechanical.

6. The device of claim 1, wherein the release mechanism is at least one of a hook, a stopper, and a pincher.

7. The device of claim 1, wherein the elastic strip comprises at least one of Ni—Ti, Cu—Al—Ni, Fe—Mn—Si, Cu—Zn—Al, and Cu—Al—Ni.

8. The device of claim 1, wherein the elastic strip is a shape-memory alloy.

* * * * *